United States Patent [19]

Foster

[11] 3,985,749
[45] Oct. 12, 1976

[54] PROCESS FOR PREPARATION OF 4-AMINOQUINAZOLINE

[75] Inventor: Charles H. Foster, Kingsport, Tenn.

[73] Assignee: Eastman Kodak Company, Rochester, N.Y.

[22] Filed: Dec. 22, 1975

[21] Appl. No.: 642,975

[52] U.S. Cl. .................................. 260/256.4 Q
[51] Int. Cl.² .................................. C07D 239/94
[58] Field of Search .................... 260/256.4 Q

[56] References Cited
UNITED STATES PATENTS

| | | | |
|---|---|---|---|
| 3,541,094 | 11/1970 | Lutz et al. | 260/256.4 Q |
| 3,560,619 | 2/1971 | Harrison et al. | 424/251 |

OTHER PUBLICATIONS

Elderfield, Heterocyclic Compounds, vol. 6, pp. 583–585, Pub. by Wiley & Sons, Inc. (1957).

*Primary Examiner*—Paul M. Coughlan, Jr.
*Attorney, Agent, or Firm*—Elliott Stern; Daniel B. Reece, III

[57] ABSTRACT

Process for preparation of a 4-aminoquinazoline which comprises the steps of 1. reacting an isatoic anhydride with an equimolar amount of ammonia in the presence of dimethyl formamide, the weight of dimethyl formamide to isatoic anhydride being from about 1:1 to about 10:1;
2. adding to the solution from about 1 to about 2 mole proportions of phosphorous oxychloride based on the amount of isatoic anhydride while maintaining the solution at a temperature of from about −10° to about 15°C.;
3. increasing the temperature of the solution to about 40° to about 55°C. and maintaining the solution in this temperature range for at least 20 minutes;
4. adding sufficient water to hydrolyze an excess phosphorous oxychloride; any
5. adding to the reaction mixture at least one mole proportion based on the amount of isatoic anhydride in step (1) of an amine and sufficient base to render the mixture neutral or basic;
6. heating the reaction mixture at a temperature from about 70° to about 100°C. for at least about 15 minutes; and
7. recovering the 4-aminoquinazoline;

These compounds are biologically active and useful, for example, in treating coccidiosis in poultry.

4 Claims, No Drawings

PROCESS FOR PREPARATION OF 4-AMINOQUINAZOLINE

This invention relates to a process for the synthesis of 4-aminoquinazolines from isatoic anhydrides. These compounds are biologically active and are useful, for example, in treating coccidiosis in poultry. See for example, U.S. Pat. No. 3,560,619. The advantages of this invention are that the process requires only a single vessel, requires no isolation of intermediates, starts with readily available materials, utilizes commercially available reagents, and produces the desired products in exceptionally high yield.

Accordingly, there is provided a process for the preparation of a 4-aminoquinazoline having the formula

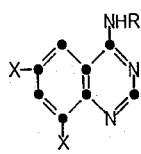

which comprises the steps of
1. reacting an isatoic anhydride having the formula

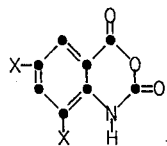

with an equimolar amount of ammonia in the presence of dimethyl formamide, the weight of dimethyl formamide to isatoic anhydride being from about 1:1 to about 10:1;
2. adding to the solution from about 1 to about 2 mole proportions of phosphorous oxychloride based on the amount of isatoic anhydride while maintaining the solution at a temperature of from about −10° to about 15° C.;
3. increasing the temperature of the solution to about 40° to about 55° C. and maintaining the solution in this temperature range for at least 20 minutes;
4. adding sufficient water to hydrolyze any excess phosphorous oxychloride;
5. adding to the reaction mixture at least one mole proportion based on the amount of isatoic anhydride in step (1) of an amine having the formula R—NH$_2$ and sufficient base to render the mixture neutral or basic;
6. heating the reaction mixture at a temperature from about 70° to about 100° C. for at least about 15 minutes; and
7. recovering the 4-aminoquinazoline;

wherein each X is the same or different and represents hydrogen, chloro, bromo or iodo; and R is hydrogen, alkyl having 1 to about 16 carbon atoms, benzyl, phenyl, m-tolyl or p-tolyl.

The isatoic anhydrides useful in this invention are readily available commercially. Preferably the isatoic anhydrides utilized are those wherein X is defined as hydrogen or chloro. In the first step of the reaction ammonia is preferably bubbled through the solution containing the isatoic anhydride and dimethylformamide solvent. Preferably the amount of dimethylformamide to isatoic anhydride will be in the average of from about 3:1 to about 7:1. The reaction may be carried out in the presence of air or in the presence of an inert atmosphere such as nitrogen. After step one a solution is obtained. Infra-red analysis of an aliquot may be used to determine the point of complete consumption of the anhydride. Any ammonium carbonate in the reactor may then be removed by passing nitrogen (N$_2$) into the solution. If desired the isatoic anhydride can be replaced as a starting material with an anthranilamide having the formula

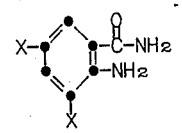

wherein X is defined as above. These compounds may be obtained commercially or prepared in a manner known in the art. In this instance step 1 comprises reacting the anthranilamide with from 1 to about 2 mole proportions of phosphorous oxychloride in the presence of dimethyl formamide, the ratio of dimethyl formamide to anthranilamide being from 1:1 to about 10:1; while maintaining the solution at a temperature of from about −10° to 15° C. The process may then be completed as described above. The anthranilamide may be obtained commercially or in a manner known in the art. After Step 1 from about 1 to about 2 mole proportions of phosphorous oxychloride is added while maintaining the solution at a temperature from about −10° to about 15° C. After addition is complete the temperature of the solution or mixture is heated from about 40° to 55° C. and maintained in this temperature range for at least about 20 minutes. After this step sufficient water should be added to the reaction mixture to hydrolyze any excess phosphorous oxychloride that may be present.

After this step at least one mole proportion of the amine based on the amount of isatoic anhydride in Step 1 is added to the reaction mixture. Preferably the amine will be either ammonia or aniline or methyl amine. During this step sufficient base is added to the reaction mixture to render the mixture neutral or basic. The base may be the amine itself or if it is advantageous, e.g., the cost of the amine being too high, one to three equivalents of an amine can be added and a solution made basic with a less expensive base such as potassium hydroxide, sodium hydroxide, sodium carbonate, potassium carbonate, sodium bicarbonate, potassium bicarbonate and the like. The next step in the reaction requires the mixture be heated from about 70° to about 100° C. for at least about 15 minutes or until the reaction is complete and then subsequently recovering the 4-aminoquinazolines in a manner known in the art, such as filtration of crystals formed on cooling.

The following examples further illustrate the invention.

EXAMPLE 1

Ammonia (NH$_3$, anhydrous) is bubbled into a slurry of 5-chloroisatoic anhydride (9.9 g., 0.05 mol.) in DMF (50 ml). When a clear solution is obtained and ir analysis of an aliquot indicates complete consumption of the anhydride, any ammonium carbonate in the reactor is then removed by passing N$_2$ into the solution. POCl$_3$ is added at 0°–15°. After addition is complete the mixture is heated 30 min. at 40°–60°, then cooled and 15–20 ml.

of H₂O is added. Ammonia is bubbled into the mixture until basic. The mixture is heated 15–20 min. at 100° C., cooled and enough H₂O added to cause the product (6-chloro-4-aminoquinazoline) to precipitate. The product is isolated by filtration, washed with water and dried (79% yield).

EXAMPLE 2

The reaction is carried out as in Example 1 except after addition of H₂O, 9.3 g. of aniline is added instead of ammonia and enough 50% NaOH to bring the pH to 7–14. The mixture is heated at reflux for 2 hr., cooled and filtered to give the desired product (6-chloro-4-anilinoquinazoline) in 51% yield.

EXAMPLES 3–6

The following compounds were prepared in a manner similar to Example 1 except the starting materials and amines utilized were varied as indicated in the following Table 1.

TABLE I

| Example | Anhydride | Amine | Product | Yield |
|---|---|---|---|---|
| 3 | Cl-[structure] | CH₃NH₂ | Cl-[structure]NHCH₃ | 66% |
| 4 | [structure] | CH₃NH₂ | [structure]NHCH₃ | 63% |
| 5 | [structure] | C₆H₅NH₂ | [structure]NHC₆H₅ | 44% |
| 6 | [structure] | NH₃ | [structure]NH₂ | 47% |

EXAMPLE 7

To a mixture of 8.5 g., (0.05 mol) of anthranilamide in 50 ml. of dimethylformamide was added POCl₃ (8.5 ml.) at 0°–15° C. The mixture was heated 30 min. at 40°–60°, then cooled to room temperature. After addition of 15–20 ml. of H₂O, ammonia was added until basic. The mixture was heated 15–20 min. at 100°, cooled and about 20 ml. of H₂O added to cause precipitation of the product.

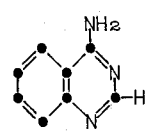

The invention has been described in detail with particular reference to preferred embodiments thereof, but it will be understood that variations and modifications can be effected within the spirit and scope of the invention.

I claim:

1. Process for preparation of a 4-aminoquinazoline having the formula

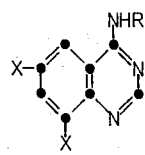

which comprises the steps of
1. reacting an isatoic anhydride having the formula

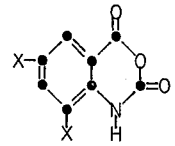

with an equimolar amount of ammonia in the presence of dimethyl formamide, the weight of dimethyl formamide to isatoic anhydride being from about 1:1 to about 10:1;

2. adding to the solution from about 1 to about 2 mole proportions of phosphorous oxychloride based on the amount of isatoic anhydride while maintaining the solution at a temperature of from about −10° to about 15° C.;

3. increasing the temperature of the solution to about 40° to about 55° C. and maintaining the solution in this temperature range for at least 20 minutes;
4. adding sufficient water to hydrolyze any excess phosphorous oxychloride;
5. adding to the reaction mixture at least one mole proportion based on the amount of isatoic anhydride in step (1) of an amine having the formula R—NH₂ and sufficient base to render the mixture neutral or basic;
6. heating the reaction mixture at a temperature from about 70° to about 100° C. for at least about 15 minutes; and
7. recovering the 4-aminoquinazoline;

wherein each X is the same or different and represents hydrogen, chloro, bromo or iodo; and R is hydrogen, alkyl having 1 to about 6 carbon atoms, benzyl, phenyl, m-tolyl or p-tolyl.

2. The process of claim 1 wherein X is hydrogen or chloro and R is hydrogen, methyl or phenyl.

3. Process for preparation of a 4-aminoquinazoline having the formula

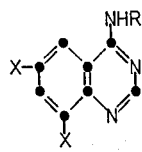

which comprises the steps of
1. reacting an anthranilamide having the formula

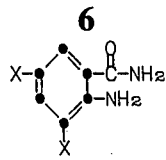

with from 1 to about 2 mole proportions of phosphorous oxychloride in the presence of dimethyl formamide, the weight of dimethyl formamide to anthranilamide being from about 1:1 to about 10:1 while maintaining the solution at a temperature of from about −10° to about 15° C.;
2. increasing the temperature of the solution to about 40° to about 55° C. and maintaining the solution in this temperature range for at least 20 minutes;
3. adding sufficient water to hydrolyze any excess phosphorous oxychloride;
4. adding to the reaction mixture at least one mole proportion based on the amount of anthranilamide in step (1) of an amine having the formula R—NH₂ and sufficient base to render the mixture neutral or basic;
5. heating the reaction mixture at a temperature from about 70° to about 100° C. for at least about 15 minutes; and
6. recovering the 4-aminoquinazoline;

wherein each X is the same or different and represents hydrogen, chloro, bromo or iodo; and R is hydrogen, alkyl having 1 to about 6 carbon atoms, benzyl, phenyl, m-tolyl or p-tolyl.

4. The process of claim 3 wherein X is hydrogen or chloro and R is hydrogen, methyl or phenyl.

* * * * *